US009125651B2

(12) United States Patent
Mandakolathur Vasudevan et al.

(10) Patent No.: US 9,125,651 B2
(45) Date of Patent: Sep. 8, 2015

(54) REUSABLE LINEAR STAPLER CARTRIDGE DEVICE FOR TISSUE THICKNESS MEASUREMENT

(75) Inventors: Venkataramanan Mandakolathur Vasudevan, Cincinnati, OH (US); Steven G. Hall, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 777 days.

(21) Appl. No.: 13/313,215

(22) Filed: Dec. 7, 2011

(65) Prior Publication Data
US 2013/0146638 A1    Jun. 13, 2013

(51) Int. Cl.
*A61B 17/068*    (2006.01)
*A61B 17/072*    (2006.01)
*A61B 19/00*    (2006.01)

(52) U.S. Cl.
CPC ..... *A61B 17/072* (2013.01); *A61B 2017/07221* (2013.01); *A61B 2017/07271* (2013.01); *A61B 2019/461* (2013.01)

(58) Field of Classification Search
CPC .............. A61B 2019/48; A61B 2019/461; A61B 5/103; A61B 5/1072; A61B 5/1075; A61B 5/1076; A61B 17/00; A61B 17/04; A61B 17/32; A61B 17/072; A61B 17/068; A61B 2017/081; A61B 2017/07271; A61B 2017/07221
USPC ............. 227/175.1–182.1, 901–902, 19; 600/587; 606/209, 153
See application file for complete search history.

(56) References Cited

U.S. PATENT DOCUMENTS

| 4,508,253 | A | * | 4/1985 | Green | 227/19 |
|---|---|---|---|---|---|
| 5,156,161 | A | * | 10/1992 | Lollar | 600/587 |
| 5,271,543 | A | | 12/1993 | Grant et al. | |
| 5,327,908 | A | * | 7/1994 | Gerry | 600/587 |
| 5,358,506 | A | * | 10/1994 | Green et al. | 606/151 |
| 5,405,073 | A | | 4/1995 | Porter | |

(Continued)

FOREIGN PATENT DOCUMENTS

| EP | 1 728 475 | 12/2006 |
|---|---|---|
| WO | WO 03/090630 | 11/2003 |

OTHER PUBLICATIONS

International Search Report dated Feb. 15, 2013 for Application No. PCT/US2012/067523.

(Continued)

*Primary Examiner* — Thanh Truong
*Assistant Examiner* — Justin Citrin
(74) *Attorney, Agent, or Firm* — Frost Brown Todd LLC (57) ABSTRACT

A surgical instrument includes a body, a removable insert including a measurement indicator, and an end effector positioned at a distal end of the body. The end effector has a distal interior surface facing a proximal end of the body. The end effector is configured to receive the insert. An actuation feature is in communication with the end effector and the insert when the insert is received in the end effector. The actuation feature is configured to advance the insert distally toward the distal interior surface of the end effector. The measurement indicator of the removable insert is configured to determine the thickness of tissue positioned between the removable insert and the distal interior surface of the end effector. Based on the measured tissue thickness, a user selects a cartridge configured to at least staple (and perhaps also sever) the measured tissue. The cartridge is received within the end effector.

17 Claims, 9 Drawing Sheets

(56) References Cited

U.S. PATENT DOCUMENTS

| | | | |
|---|---|---|---|
| 5,452,836 A | 9/1995 | Huitema et al. | |
| 5,462,215 A * | 10/1995 | Viola et al. | 227/176.1 |
| 5,465,894 A | 11/1995 | Clark et al. | |
| 5,533,521 A * | 7/1996 | Granger | 600/587 |
| 5,603,443 A | 2/1997 | Clark et al. | |
| 5,605,272 A | 2/1997 | Witt et al. | |
| 5,607,094 A | 3/1997 | Clark et al. | |
| 5,697,543 A | 12/1997 | Burdorff | |
| 5,732,871 A | 3/1998 | Clark et al. | |
| 5,810,240 A * | 9/1998 | Robertson | 227/175.2 |
| 5,865,361 A * | 2/1999 | Milliman et al. | 227/176.1 |
| 5,878,937 A * | 3/1999 | Green et al. | 227/175.2 |
| 6,805,273 B2 * | 10/2004 | Bilotti et al. | 227/180.1 |
| 6,988,650 B2 | 1/2006 | Schwemberger et al. | |
| 7,134,587 B2 | 11/2006 | Schwemberger et al. | |
| 7,188,758 B2 * | 3/2007 | Viola et al. | 227/180.1 |
| 7,204,404 B2 | 4/2007 | Nguyen et al. | |
| 7,207,472 B2 | 4/2007 | Wukusick et al. | |
| 7,717,312 B2 * | 5/2010 | Beetel | 227/175.1 |
| 7,766,207 B2 | 8/2010 | Mather et al. | |
| 8,062,236 B2 | 11/2011 | Soltz | |
| 2004/0094597 A1 * | 5/2004 | Whitman et al. | 227/180.1 |
| 2005/0131390 A1 * | 6/2005 | Heinrich et al. | 606/1 |
| 2007/0179408 A1 * | 8/2007 | Soltz | 600/587 |
| 2009/0012556 A1 * | 1/2009 | Boudreaux et al. | 606/206 |
| 2009/0209946 A1 * | 8/2009 | Swayze et al. | 606/1 |
| 2010/0200637 A1 * | 8/2010 | Beetel | 227/175.1 |

OTHER PUBLICATIONS

International Preliminary Report on Patentability dated Jun. 10, 2014 for Application No. PCT/US2012/067523.

* cited by examiner

REUSABLE LINEAR STAPLER CARTRIDGE DEVICE FOR TISSUE THICKNESS MEASUREMENT

BACKGROUND

In some settings, surgical instruments include distal end effectors suitable for placement at a desired surgical site such as, for example, at tissue to be severed and/or stapled. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Such surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of such surgical instruments include surgical staplers. Some such staplers are operable to clamp down on layers of tissue, to sever the clamped layers of tissue, and to drive staples through the layers of tissue to substantially seal the severed layers of tissue together near the severed ends of the tissue layers. Merely exemplary surgical staplers are disclosed in U.S. Pat. No. 5,271,543, entitled "Surgical Anastomosis Stapling Instrument with Flexible Support Shaft and Anvil Adjusting Mechanism," issued Dec. 21, 1993, the disclosure of which is incorporated by reference herein; U.S. Pat. No. 5,405,073, entitled "Flexible Support Shaft Assembly," issued Apr. 11, 1995, the disclosure of which is incorporated by reference herein; U.S. Pat. No. 5,452,836, entitled "Surgical Stapling Instrument with Improved Jaw Closure and Staple Firing Actuator Mechanism," issued Sep. 26, 1995, the disclosure of which is incorporated by reference herein; U.S. Pat. No. 5,465,894, entitled "Surgical Stapling Instrument with Articulated Stapling Head Assembly on Rotatable and Flexible Support Shaft," issued Nov. 14, 1995, the disclosure of which is incorporated by reference herein; U.S. Pat. No. 5,603,443, entitled "Surgical Stapling Instrument with Articulated Stapling Head Assembly on Rotatable and Flexible Support Shaft," issued Feb. 18, 1997, the disclosure of which is incorporated by reference herein; U.S. Pat. No. 5,605,272, entitled "Trigger Mechanism for Surgical Instruments," issued Feb. 25, 1997, the disclosure of which is incorporated by reference herein; U.S. Pat. No. 5,607,094, entitled "Surgical Stapling Instrument with Articulated Stapling Head Assembly on Rotatable and Flexible Support Shaft," issued Mar. 4, 1997, the disclosure of which is incorporated by reference herein; U.S. Pat. No. 5,697,543, entitled "Linear Stapler with Improved Firing Stroke," issued Dec. 16, 1997, the disclosure of which is incorporated by reference herein; U.S. Pat. No. 5,732,871, entitled "Surgical Stapling Instrument with Articulated Stapling Head Assembly on Rotatable and Flexible Support Shaft," issued Mar. 31, 1998, the disclosure of which is incorporated by reference herein; U.S. Pat. No. 6,988,650, entitled "Retaining Pin Lever Advancement Mechanism for a Curved Cutter Stapler," issued Jan. 24, 2006, the disclosure of which is incorporated by reference herein; U.S. Pat. No. 7,134,587, entitled "Knife Retraction Arm for a Curved Cutter Stapler," issued Nov. 14, 2006, the disclosure of which is incorporated by reference herein; U.S. Pat. No. 7,204,404, entitled "Slotted Pins Guiding Knife in a Curved Cutter Stapler," issued Apr. 17, 2007, the disclosure of which is incorporated by reference herein; U.S. Pat. No. 7,207,472, entitled "Cartridge with Locking Knife for a Curved Cutter Stapler," issued Apr. 24, 2007, the disclosure of which is incorporated by reference herein; and U.S. Pat. No. 7,766,207, entitled "Articulating Curved Cutter Stapler," issued Aug. 3, 2010, the disclosure of which is incorporated by reference herein.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Linear Surgical Stapler

Figure 2:
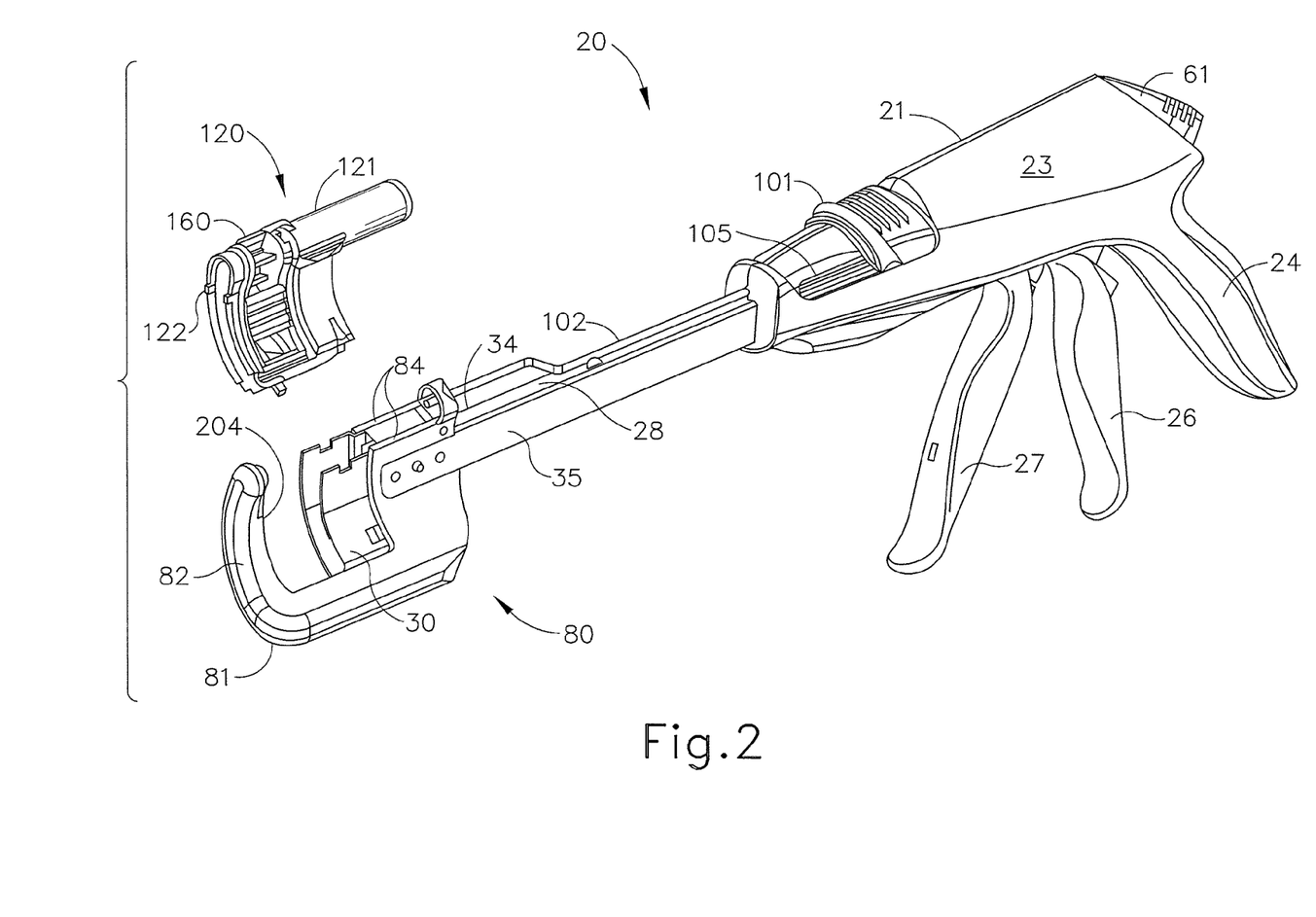
FIG. 2 depicts a perspective view of the linear surgical stapler of FIG. 1 with the cartridge module removed.
Figure 3:
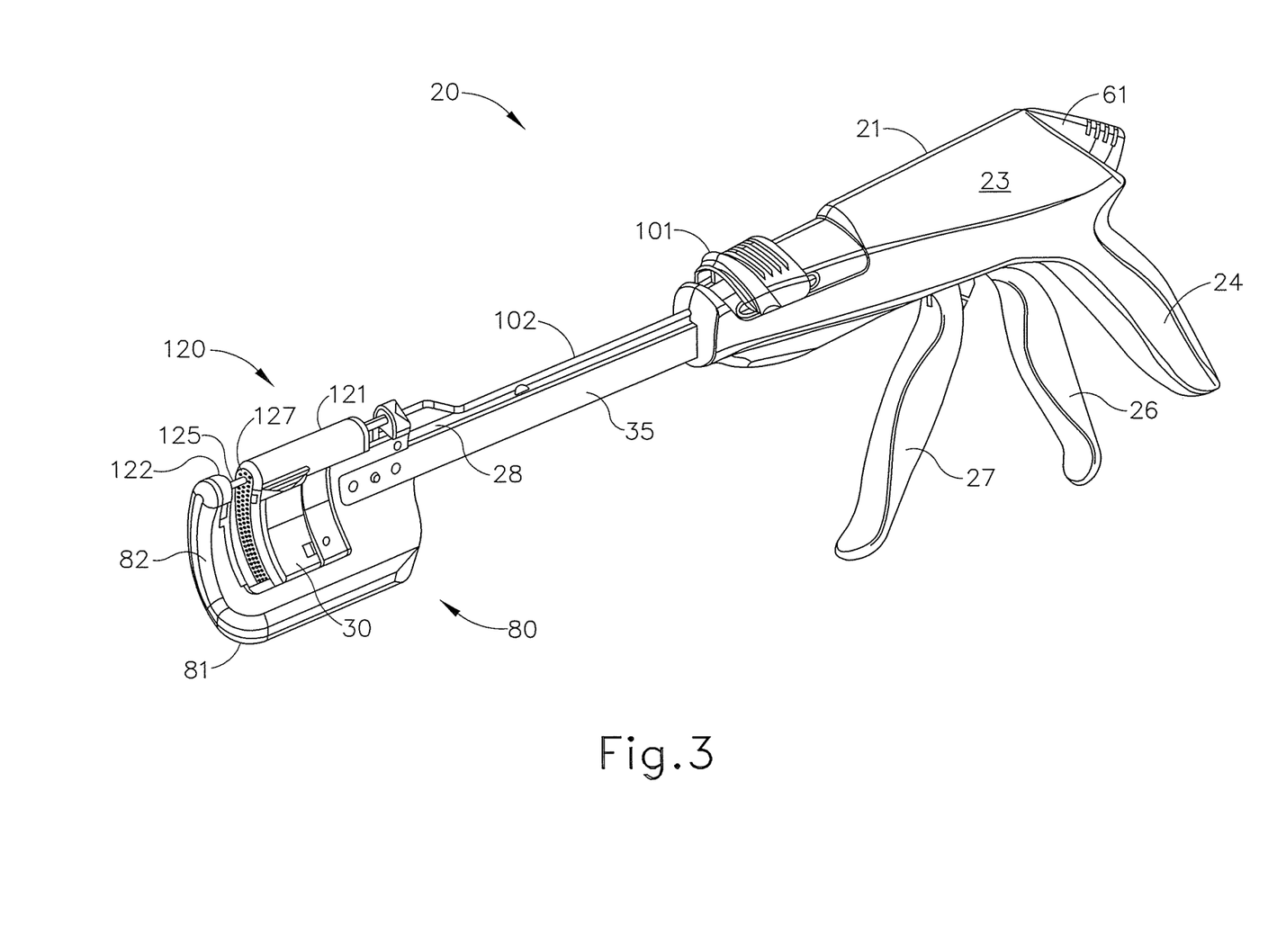
FIG. 3 depicts a perspective view of the linear surgical stapler of FIG. 1 with the cartridge housing moved to an intermediate position.
Figure 4:
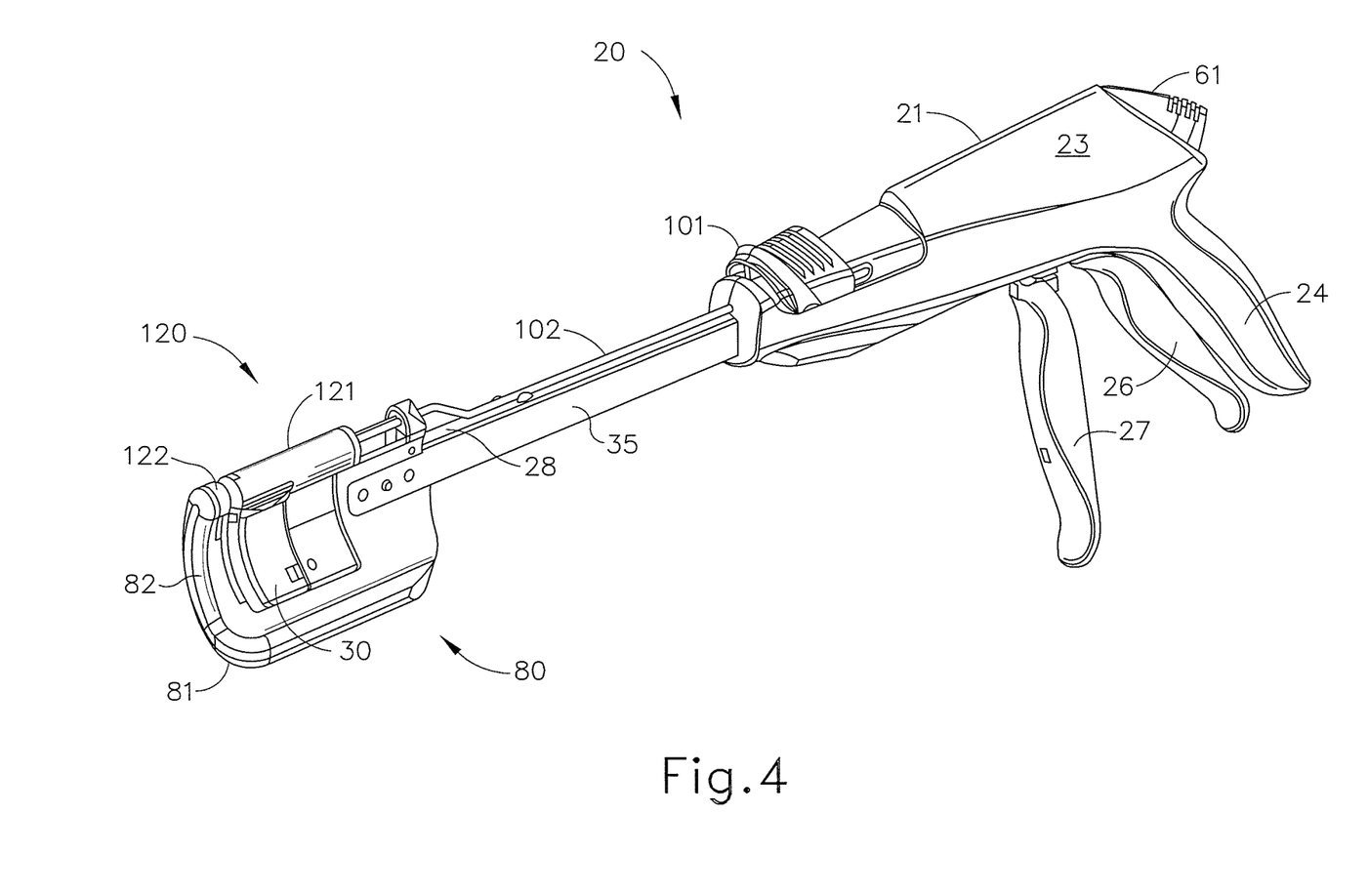
FIG. 4 depicts a perspective view of the linear surgical stapler of FIG. 1 with the cartridge housing moved to a closed position.

FIGS. 1-6 show an exemplary linear surgical stapler or surgical instrument (20) adapted for applying a plurality of surgical fasteners to body tissue. Surgical instrument (20) includes a frame having a proximal end and a distal end, with a handle (21) positioned at the proximal end and an end effector (80) positioned at the distal end. End effector (80) is shaped and dimensioned for supporting a cartridge housing (121) and an anvil (122). Cartridge housing (121) and anvil (122) are relatively movable between a first spaced apart position (FIG. 1) and a second position in close approximation with one another (FIG. 4). Instrument (20) also includes a firing assembly associated with end effector (80) and cartridge housing (121) for selective actuation of the fasteners. The instrument further includes a retaining pin (125) (see FIG. 3) for enclosing tissue between anvil (122) and cartridge housing (121). Retaining pin (125) is movable relative to cartridge housing (121) under the control of a retaining pin actuation assembly (100). Retaining pin actuation assembly (100) includes a yoke (111) (see FIGS. 5-6) rotationally connected to handle (21) for facilitating both manual and automatic advancement of retaining pin (125) and requiring manual retraction of retaining pin (125).

Figure 1:
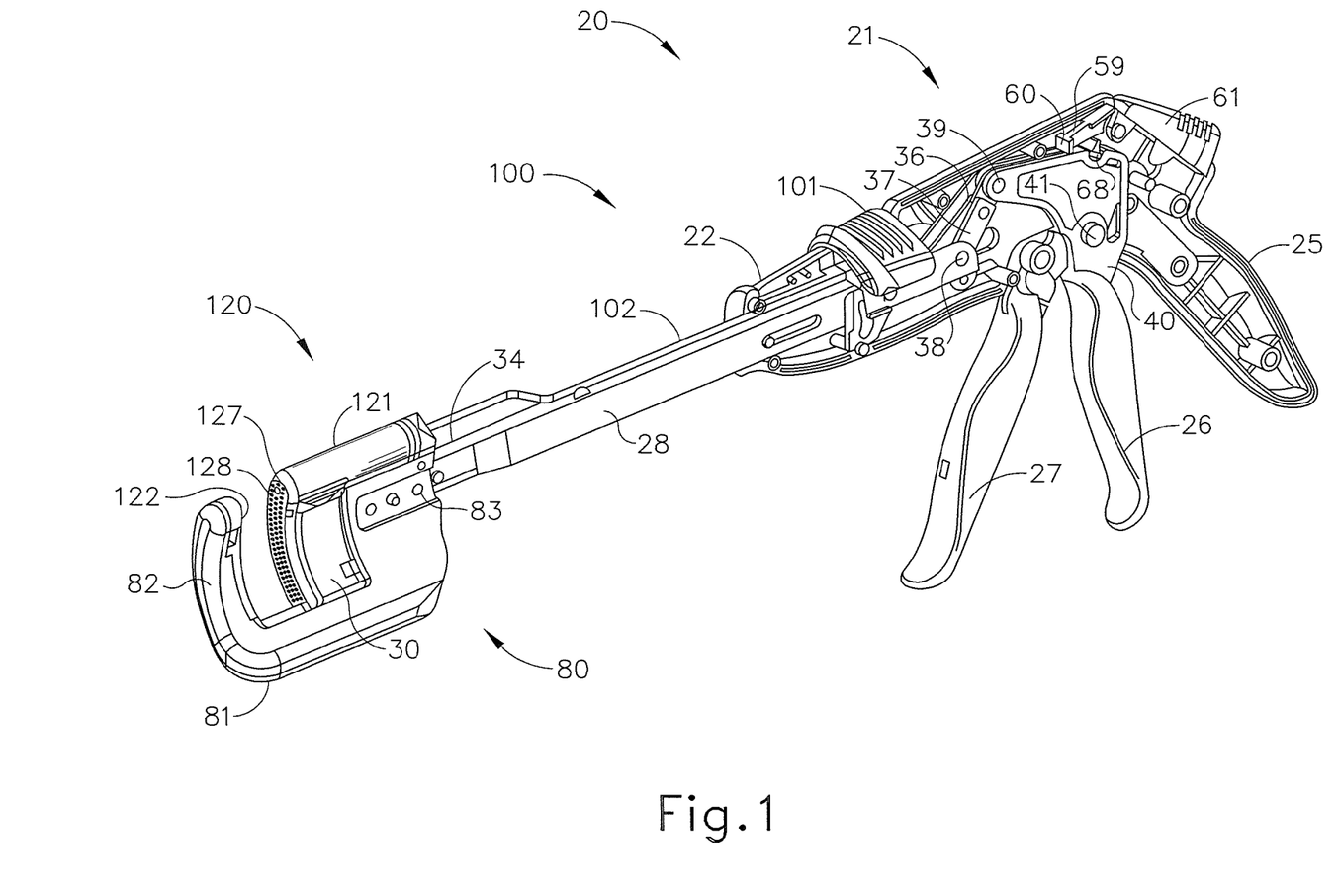
FIG. 1 depicts a perspective view of a linear surgical stapler having a cartridge housing and a cartridge module.

Right and left hand structural plates (34, 35) connect handle (21) to end effector (80) of the instrument (the left hand structural plate (35) is not shown in FIG. 1). Handle (21) has a right hand shroud (22) coupled to a left hand shroud (the left hand shroud is not shown in FIG. 1). Handle (21) also has a body portion (23) to grip and maneuver surgical instrument (20) (see FIGS. 2 to 4).

While end effector (80) is curved in the present example, end effector (80) may alternatively be straight or have another shape as taught in accordance with any of the references cited herein. End effector (80) is a surgical fastening assembly that includes a cartridge module (120) (see FIG. 2) and a C-shaped supporting structure (81). Supporting structure (81) may alternatively be another shape as apparent to one of ordinary skill in the art in view of the teachings herein such that supporting structure (81) is configured to receive a corresponding alternatively shaped cartridge module (120). A distal end (30) of a closure member (28) is disposed to engage cartridge module (120).

Cartridge module (120) contains cartridge housing (121) coupled to anvil (122). The cartridge module (120) also includes a retaining pin (125) (see FIG. 3), a knife (not shown), a removable retainer (160) (see FIG. 2), a tissue contacting surface (127) (see FIG. 1) that includes a plurality of staple-containing slots (128) in staggered formation in one or more rows (that is, staple lines) on either side of the knife. Staples (not shown) are fired from cartridge housing (121) against a staple-forming surface of anvil (122) that faces tissue-contacting surface (127) of cartridge housing (121).

A shoulder rivet (82) extends from supporting structure (81) of end effector (80). Supporting structure (81) is respectively attached to right and left structural plates (34, 35), by posts (83), which extend from supporting structure (81) for receipt within receiving holes defined in structural plates (34, 35). By way of example only, supporting structure (81) may be constructed in accordance with the teachings of U.S. Pat. No. 6,988,650, entitled "Retaining Pin Lever Advancement Mechanism for a Curved Cutter Stapler," issued Jan. 24, 2006, the disclosure of which is incorporated by reference herein.

Handle (21) of surgical instrument (20) includes a hand grip (24) that the surgeon grasps with the palm of his hand (see FIG. 2). Hand grip (24) is composed of a right hand shroud handle (25) (see FIG. 1) and a left hand shroud handle (the left hand shroud handle is not shown in FIG. 1). A closure trigger (26) and a firing trigger (27) pivotally extend from the underside of handle (21). Surgical instrument (20) illustrated in FIG. 1 is shown with respective closure and firing triggers (26, 27) in their unactuated positions and with cartridge module (120) inserted and retainer (160) (see FIG. 2) removed. Consequently, cartridge housing (121) is spaced from anvil (122) for the placement of tissue between cartridge housing (121) and anvil (122).

Figure 5:
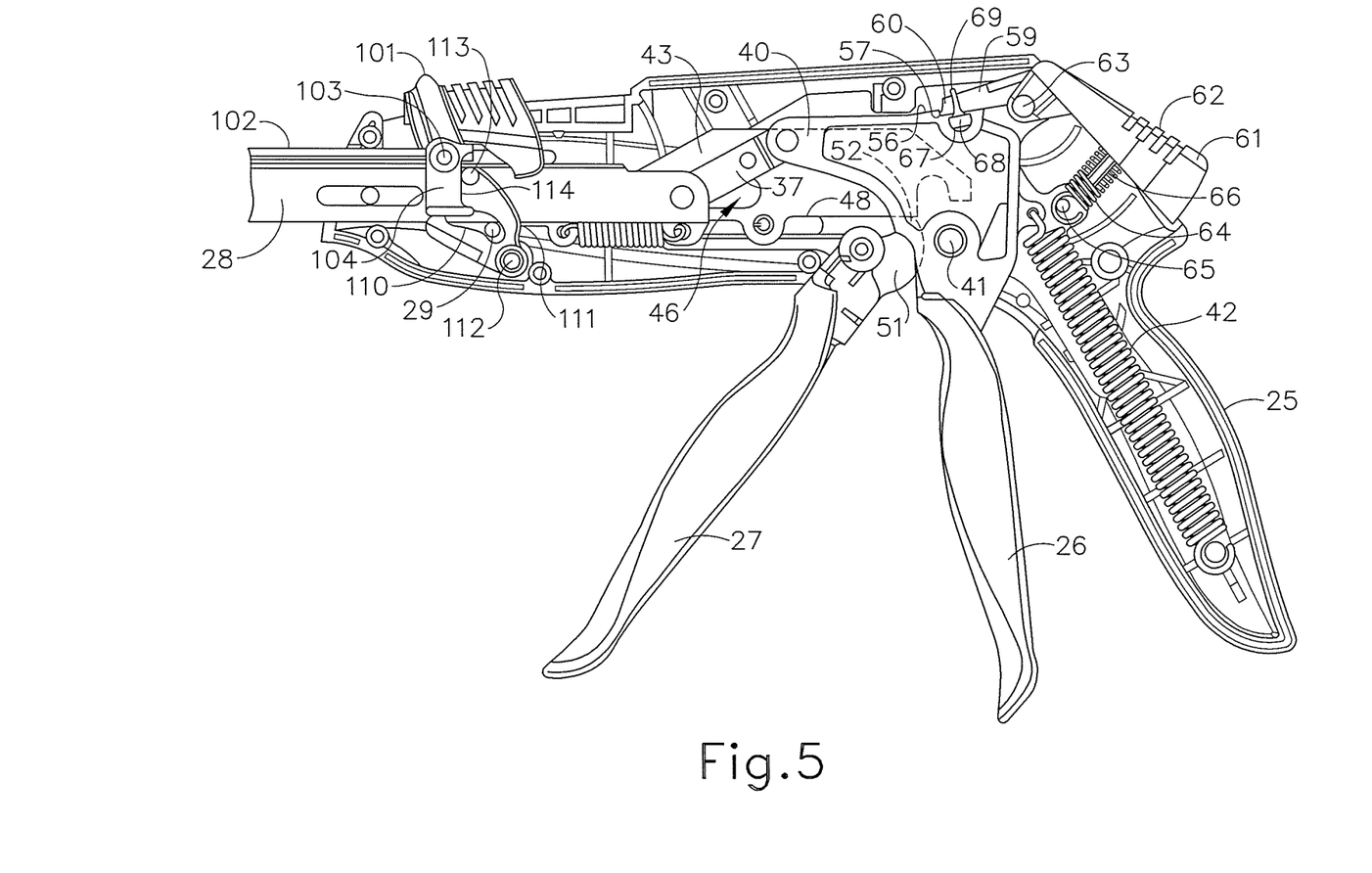
FIG. 5 depicts a partial cross-sectional view of the linear surgical stapler with a closure trigger slightly retracted.
Figure 6:
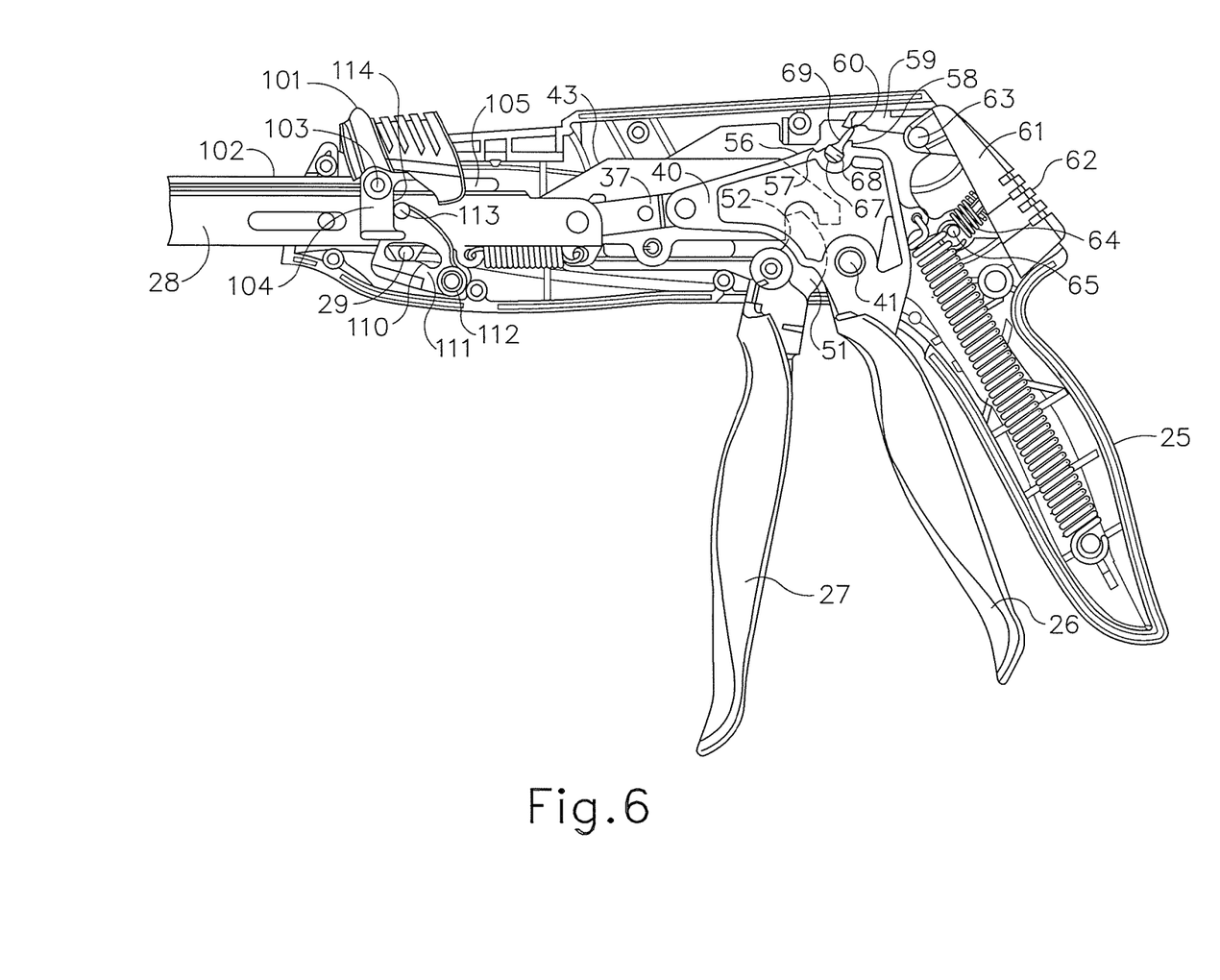
FIG. 6 depicts a partial cross-sectional view of the linear surgical stapler with the closure trigger nearly fully retracted.

Handle (21) of surgical instrument (20) contains tissue retaining pin actuation assembly (100). Retaining pin (125) is associated with retaining pin actuation assembly (100) for advancing retaining pin (125) through cartridge housing (121) and into anvil (122) to thereby capture tissue. By way of example only, retaining pin (125) is constructed and operable in accordance with the teachings of U.S. Pat. No. 6,988,650, the disclosure of which is incorporated by reference above. Tissue retaining pin actuation assembly (100) includes a saddle shaped slide (101) that is positioned on the top surface of handle (21) and is in communication with push rod (102), as described below. Manual movement of slide (101) results in distal movement of a push rod (102). Push rod (102) is coupled via a coupler (not shown) to retaining pin (125) of cartridge module (120). The distal movement or proximal retraction of push rod (102) results in corresponding longitudinal movement of retaining pin (125). In particular, and as shown in FIGS. 5 and 6, slide (101) is connected to a post (103) that extends outward from a push rod driver (104) through slots (105) (see FIG. 2) in the handle (21). Push rod driver (104) is restrained for longitudinal movement along a long axis of surgical instrument (20) by slots (105). Push rod driver (104) is connected to push rod (102) by a circumferential groove on push rod (102) that snaps into a slot of push rod driver (104). A distal end of the push rod (102) contains a circumferential groove that interconnects with a groove in a proximal end of the coupler (not shown) of cartridge module (120). A distal end of the coupler contains a groove for interconnecting with a circumferential slot on retaining pin (125).

As shown in FIGS. 1 and 2, surgical instrument (20) further includes an elongated closure member (28), which has a generally U shaped cross section. Closure member (28) extends from handle (21) into the surgical fastening assembly of end effector (80). By way of example only, closure member (28) may be constructed in accordance with the teachings of U.S. Pat. No. 6,988,650, the disclosure of which is incorporated by reference above. Closure member (28) contains posts (29) (see FIG. 5) that extend laterally on both sides of closure member (28) inside handle (21). These posts (29) slidably connect to an L-shaped slot (110) of a yoke (111), which is part of retaining pin actuation assembly (100) as described below. Yoke (111) is pivotally mounted to handle (21) by a pivot pin (112) on yoke (111). The yoke (111) contains cam pins or posts (113) positioned to push camming surfaces (114) on push rod driver (104).

A distal portion of closure member (28) passes through walls (84) (see FIG. 2) of supporting structure (81). A distal end of closure member (28) is disposed to receive and retain cartridge housing (121) of the cartridge module (120). A central portion of closure member (28) is positioned between right and left structural plates (34, 35), respectively. Right and left hand closure links (36, 37), respectively, are pivotally attached at right and left proximal ends of closure member (28) by a first integral closure link pin (38). At the opposite end of closure links (36, 37), closure links (36, 37) are pivotally attached to a second integral closure link pin (39). Second integral closure link pin (39) connects closure links (36, 37) to a slotted closure arm link (40). Slotted closure arm link (40)

is pivotally mounted to structural plates (34, 35) of surgical instrument (20) at a closure trigger pivot pin (41). Closure trigger (26) descends from slotted closure arm link (40) for pivotal rotation about closure trigger pivot pin (41) toward and away from hand grip (24). A closure spring (42) (see FIG. 5) housed within hand grip (24) of handle (21) is secured to slotted closure arm link (40) to provide a desired resistance when the surgeon squeezes closure trigger (26) toward hand grip (24), and to bias closure trigger (26) toward the open position.

Retaining pin actuation assembly (100) is also releasably coupled to closure trigger (26) within handle (21) such that actuation of closure trigger (26) will result in automatic distal movement of retaining pin (125) if it has not already been manually moved to its most distal position. In particular, during instrument actuation, closure member (28) moves linearly, rotating yoke (111) that advances retaining pin (125). By way of example only, yoke (111) is constructed and operable in accordance with the teachings of U.S. Pat. No. 6,988,650, the disclosure of which is incorporated by reference above. Yoke (111) does not communicate with slide (101), and thus yoke (111) or slide (101) may separately operate as described above to distally move retaining pin (125).

By way of example only, the operation of loading the cartridge module (120) into end effector (80) may occur in accordance with the teachings of U.S. Pat. No. 6,988,650, the disclosure of which is incorporated by reference above. For example, cartridge housing (121) connects to a distal end of closure member (28) in a snap-fit connection, such that when closure member (28) distally advances, as further described below, attached cartridge housing (121) will distally advance if retainer (160) has been removed and is not restricting cartridge housing (121). FIGS. 2 to 4 illustrate what happens when cartridge module (120) is loaded and respective closure and firing triggers (26, 27) are sequentially squeezed toward hand grip (24) to actuate end effector (80) of surgical instrument (20). Surgical instrument (20) is loaded with cartridge module (120), as shown in FIG. 2, and retainer (160) is removed. Surgical instrument (20) is now ready to receive tissue, as shown in FIG. 1.

When closure trigger (26) is partially squeezed to rest in its first detent position shown in FIG. 3, cartridge housing (121) moves from its fully opened position to an intermediate position between the open and closed positions. Simultaneously, tissue retaining pin actuation assembly (100) moves retaining pin (125) distally forward from cartridge housing (121) to pierce through clamped tissue and then enter an opening in anvil (122), thus retaining the pierced and clamped tissue. In this position, tissue that has been placed between cartridge housing (121) and anvil (122) can be properly positioned, and the retention of the tissue between cartridge housing (121) and anvil (122) is assured. Therefore, when closure trigger (26) has been actuated to its intermediate position, cartridge housing (121) and anvil (122) are correspondingly positioned in their tissue retaining positions.

When closure trigger (26) is fully squeezed so that it is adjacent the forward end of hand grip (24), as illustrated in FIG. 4, tissue contacting surface (127) of cartridge housing (121) and the staple-forming surface of anvil (122) are adjacent to each other, and the properly positioned and retained tissue is consequently fully clamped. Additionally, firing trigger (27) has rotated counterclockwise toward hand grip (24) to enable the surgeon to grasp firing trigger (27) for the firing of staples. Accordingly, firing trigger (27) is now in position for the surgeon to squeeze it to staple and cut the clamped tissue substantially simultaneously. When firing trigger (27) has been fully squeezed to fire the staples, the firing trigger (27) rests in near proximity to the closure trigger (26).

In operation, when closure trigger (26) is squeezed toward hand grip (24), slotted closure arm link (40), and closure links (36), move distally within a receiving slot (46) of firing bar (43). By way of example only, firing bar (43) may be constructed and operable in accordance with the teachings of U.S. Pat. No. 6,988,650, the disclosure of which is incorporated by reference above. The distal movement of slotted closure arm link (40) and closure link (36) causes closure member (28) to correspondingly move distally. Likewise, firing bar (43) concurrently moves distally with closure member (28) because first integral closure link pin (38) (see FIG. 1), to which closure links (36, 37) are attached, extends through receiving slot (46) in firing bar (43).

The assembly that defines an intermediate closure detent position and the release of closure trigger (26) from an actuated position to its original unactuated position will now be described in connection with FIG. 1 in combination with FIGS. 5 and 6. The top side of slotted closure arm link (40) has a clamp sliding surface (56) that displays an intermediate detent (57) and a closure detent (58). A release pawl (59) slides on clamp sliding surface (56) and may engage respective intermediate and closure detents (57, 58). Release pawl (59) has a laterally extending pawl lug (60) (see FIGS. 1 and 5) at its distal end. Release pawl (59) is located within handle (21), and it is integrally attached to a release button (61) situated exteriorly of handle (21). Release button (61) has a thumb rest (62) (see FIG. 5), and release button (61) is pivotally attached to handle (21) by a release trunnion or pivot (63). Release button (61) is biased outwardly from handle (21). Thus, release pawl (59) is biased downwardly toward clamp sliding surface (56) by a release spring (64). Release spring (64) is mounted to handle (21) by a spring retention pin (65) and is mounted to release button (61) by a button spring post (66). Slotted closure arm link (40) has an arcuate recess (67) located between respective intermediate and closure detents (57, 58). Sitting within this arcuate recess (67) for rotational movement are a left hand toggle (68) integrally connected to a right hand toggle (the right hand toggle is not shown). Each toggle (68) has a toggle arm (69) that is engageable with pawl lug (60). By way of example only, pawl lug (60) is constructed and operable in accordance with the teachings of U.S. Pat. No. 6,988,650, the disclosure of which is incorporated by reference above.

In FIG. 5, closure trigger (26) has been partially squeezed from its open, unactuated position illustrated in FIG. 1. When closure trigger (26) is partially squeezed, it pivots about closure trigger pivot pin (41) in a counterclockwise direction toward hand grip (24). As it pivots, slotted closure arm link (40) and closure plate closure links (36, 37) move distally forward, consequently moving closure member (28) and firing bar (43) distally. As slotted closure arm link (40) moves distally, pawl lug (60) of release pawl (59) proximally slides on clamp sliding surface (56). Pawl lug (60) engages the distal ends of toggle arms (69) of toggles (68), and consequently pivots toggles (68) in a clockwise direction. As slotted arm closure link (40) continues to move distally in response to the pivotal movement of closure trigger (26) toward hand grip (24), pawl lug (60) of release pawl (59) will eventually lodge into intermediate detent (57). Once positioned in intermediate detent (57), closure spring (42) is incapable of returning closure trigger (26) to its original, unactuated position. Closure trigger (26) is now in its intermediate, partially closed position, to properly position and retain tissue between cartridge housing (121) and anvil (122), as shown in FIG. 5. In addition, as closure member (28) and firing bar (43) move distally, an apex (52) of an arcuate firing trigger link (51) slides on a sliding surface (48) of firing bar (43) toward a proximal end section of firing bar (43).

Retaining pin actuation assembly (100) is activated during the closing stroke from the open to the intermediate position. Forward movement of closure member (28) moves integral posts (29) distally. Posts (29) contact L-shaped slot (110) of yoke (111). Hence, distal movement of posts (29) cam L-shaped slot (110) causes yoke (111) to pivot around pins (112). The rotation brings bearing posts (113) on yoke (111) into contact with camming surfaces (114) on push rod driver (104). Further rotational movement of yoke (111) causes bearing posts (113) to move push rod driver (104) distally through camming contact on surfaces (114). Push rod driver (104) contacts push rod (102), moving push rod (102) distally. Push rod (102), in turn, moves the coupler and retaining pin (125) distally. Completion of the closing stroke to intermediate detent (57) position results in retaining pin (125) moving distally through the hole (not shown) of cartridge housing (121), through hole (159) running through a washer (not shown) and anvil (122) and into a hole (not shown) in supporting structure (81). Tissue, which was disposed between tissue contacting surface (127) of cartridge housing (121) and anvil (122), is now trapped between retaining pin (125) and guide pin (124).

By way of example only, this same result can be obtained prior to closing by manual distal movement of saddle shaped slide (101) in accordance with the teachings of U.S. Pat. No. 6,988,650, the disclosure of which is incorporated by reference above.

Referring now specifically to FIG. 6, when closure trigger (26) is squeezed toward hand grip (24) from intermediate detent (57) position, toggle arms (69) of toggle (68) disengage from pawl lug (60). Consequently, as toggle (68) continues to rotate in a clockwise direction, release pawl lug (60) rides up toggle arms (69) and with continued motion of closure trigger (26) falls into closure detent (58). As release pawl (59) rides up toggle arm (69), it rotates release button (61) clockwise around pivot (63). As release pawl lug (60) falls into closure detent (58), it makes an audible clicking sound alerting the surgeon that closure position has been reached.

In addition, as firing bar (43) continues to move distally forward, apex (52) of arcuate firing trigger link (51) comes into contact with a side engagement surface of the proximal end section of firing bar (43). Consequently, the firing trigger (27) is moving into a position where it can continue to move firing bar (43) distally to fire staples after the tissue has been fully clamped. When apex (52) of arcuate firing trigger link (51) moves into engagement with the engagement surface of the proximal end section of firing bar (43), firing trigger (27) begins to pivotally rotate in a counterclockwise direction toward hand grip (24) in response to the action of a torsion spring on the right hand side of firing trigger (27) (torsion spring not shown). Firing trigger (27) pivots independently of the pivotal movement of closure trigger (26), but its pivotal rotation is blocked until firing bar (43) has moved distally to enable engagement of firing trigger link (51) with a terminal engagement surface of firing bar (43). The firing of the staples may, by way of example only, occur in accordance with the teachings of U.S. Pat. No. 6,988,650, the disclosure of which is incorporated by reference above. Various other suitable ways in which instrument (20) may be configured and operable will be apparent to one of ordinary skill in the art in view of the teachings herein.

II. Exemplary Removable Cartridge Device for Tissue Thickness Measurement

Examples described below relate to connections and uses of removable cartridges with end effector portions of linear surgical stapler and/or cutter instruments, such as instrument (20), to measure tissue thickness. For instance, the tissue thickness measurement cartridges described below may be used to measure the thickness of tissue that is positioned between the cartridge and an interior surface (204) of shoulder rivet (82), simply by squeezing closure trigger (26) toward handle (25). Various suitable ways in which the below teachings may be incorporated into instrument (20) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (20) or devices taught in the references cited herein. The below teachings may be readily applied to various other kinds of instruments, including instruments that would not be classified as linear surgical stapler instruments. Various other suitable devices and settings in which the below teachings may be applied will be apparent to those of ordinary skill in the art in view of the teachings herein.

A. Exemplary Removable Cartridge Device with a Metal Plate Assembly

Figure 7:
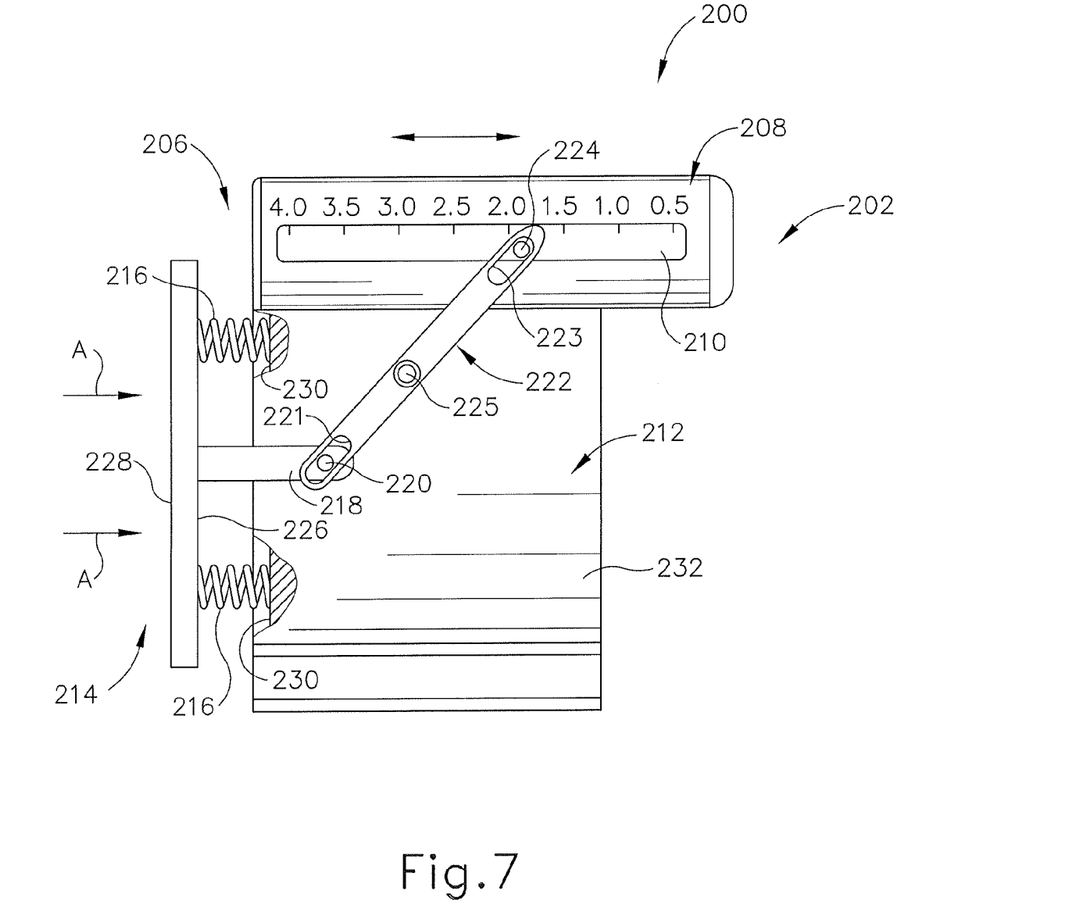
FIG. 7 depicts a side elevation view of an exemplary removable cartridge device to measure tissue thickness.

FIG. 7 shows an exemplary removable cartridge device (200) configured for receipt into end effector (80) of instrument (20). For instance, cartridge device (200) may couple with end effector (80) in a manner similar to the receipt of cartridge module (120) in accordance with the teachings of U.S. Pat. No. 6,988,650, the disclosure of which is incorporated by reference above. In the present example, a cartridge device (200) includes a shape similar to the shape of cartridge housing (121) of cartridge module (120) other than as set forth below. Alternatively, cartridge device (200) may include any shape apparent to one of ordinary skill in the art in view of the teachings herein. Cartridge device (200) may be sterilized as apparent to one of ordinary skill in the art in view of the teachings herein and may be reused in multiple uses. Cartridge device (200) may be constructed from a durable plastic (such as polycarbonate or a liquid crystal polymer), ceramics, metals, and/or any other suitable material as will be apparent to one of ordinary skill in the art in view of the teachings herein. Other configurations for cartridge device (200) will also be apparent to those of ordinary skill in the art in view of the teachings herein.

Cartridge device (200) will form a snap-fit connection with the distal end of closure member (28) when loaded into end effector (80), similar to the manner in which cartridge housing (121) forms a snap-fit connection with a distal end of closure member (28). Still other configurations for the attachment of cartridge device (200) to closure member (28) will be apparent to one of ordinary skill in the art in view of the teachings herein. Closure member (28) may include a variety of components or features that are operable to removably secure cartridge device (200) to end effector (80).

Referring to FIG. 2 in combination with FIG. 7, push rod (102) may be coupled to an upper proximal portion (202) of cartridge device (200) such that a distal advance of push rod (102), by squeezing closure trigger (26) in a manner as described above with respect to instrument (20), will result in a distal advance of cartridge device (200) toward interior surface (204) of shoulder rivet (82). Further, as the distal end of closure member (28) is connected to cartridge device (200) when cartridge device (200) is loaded into end effector (80), as described above, a distal advance of closure member (28)

will additionally distally advance cartridge device (200) toward interior surface (204) of end effector (80).

As shown in FIG. 7, cartridge device (200) includes upper proximal portion (202) and an opposing, distal portion (206). A measurement display (210) is disposed along an upper edge portion (208) between upper proximal portion (202) and distal portion (206). While the present example shows measurement display (210) as including measurements of 0.5 increments on a graduated scale ranging from 0 to 4.0, other measurement increments may be displayed. The increments may be values or units measureable in inches, centimeters, millimeters, or other units apparent to those of ordinary skill in the art in view of the teachings herein. Measurement display (210) is part of and is connected to a mechanical gauge assembly (212), described below.

Mechanical gauge assembly (212) includes plate (214), springs (216), horizontal linkage (218) acting as a mechanical transducer, pin (220), linkage slot (221), pivotable linkage (222), slot (223), pin (224), and pivot pin (225). Plate (214) may comprise metal, plastic, or any other suitable material apparent to those of ordinary skill in the art in view of the teachings herein. While the present example includes springs as biasing members, springs (216) may alternatively be any other suitable biasing member apparent to those of ordinary skill in the art in view of the teachings herein.

Plate (214) includes a proximal surface (226) and a distal surface (228). Outwardly biased springs (216) resiliently connect proximal surface (226) of plate (214) to a surface (230) of distal portion (206) of cartridge device (200). Springs (216) bias plate (214) away from housing (232) of cartridge device (200). Horizontal linkage (218) proximally extends from proximal surface (226) of plate (214) and includes pin (220) projecting from a proximal end of horizontal linkage (218) in a direction substantially perpendicular to a longitudinal axis of horizontal linkage (218). Pin (220) is retained within and slidable along a horizontal retaining slot (not shown) disposed in housing (232) of cartridge device (200). Alternatively, pin (220) may be disposed within an aperture that is disposed in housing (232) and is sized and configured to receive pin (220). In the present example, the horizontal retaining slot that receives pin (220) is substantially parallel to and aligned with the longitudinal axis of horizontal linkage (218). Pin (220) is also received within slot (221) at a lower end of pivotable linkage (222). Pivot pin (225) is disposed between upper and lower ends of pivotable linkage (222), and pivotable linkage (222) is configured to pivot about pivot pin (225). At a zero pressure position, in which pressure has not yet been applied to distal surface (228) of plate (214) as described below, pivotable linkage (222) will stand in a substantially angled position with respect to horizontal linkage (218). An upper end of pivotable linkage (222) will be positioned at a proximal end of measurement display (210), indicating zero units of pressure and a zero measurement of thickness (indicating no tissue is currently clamped for measurement). At its upper end, pivotable linkage (222) includes slot (223) that receives pin (224). Pin (224) is received and is slidable within a horizontal measurement display slot (not shown) spanning a longitudinal axis of measurement display (210).

In operation, when cartridge device (200) is loaded into end effector (80) as described above, tissue (not shown) may be positioned between distal surface (228) of plate (214) of cartridge device (200) and interior surface (204) of end effector (80). Cartridge device (200) may be distally advanced toward interior surface (204) of end effector (80) in a manner as described above with respect to cartridge housing (121) until the tissue is disposed between and contacting both distal surface (228) of plate (214) and interior surface (204) of end effector (80). For example, retaining pin (125) may pierce and retain tissue between plate (214) and interior surface (204) of end effector (80) in the manner described above for cartridge housing (121).

As cartridge device (200) is distally advanced against the tissue, the tissue will compress against distal surface (228) of plate (214), causing plate (214) to compress springs (216) in the direction of arrow (A) in toward surface (230) of distal portion (206) of cartridge device (200). This in turn will move horizontal linkage (218) proximally inward, sliding pin (220) proximally along the horizontal retaining slot in cartridge device (200). As pin (220) slides horizontally inward along the retaining slot, pin (220) will concurrently press against surfaces defining slot (221) of pivotable linkage (222), causing pivotable linkage (222) to pivot about pin (220) and pivot pin (225) in a counter-clockwise direction. Such pivotal motion advances pin (224) distally along the horizontal measurement display slot spanning at least the length of measurement display (210). The lengths of slots (221, 223) are sufficient to allow for the height adjustability needed between pins (220, 224) at a first position and at a second, different position. The action of distally advancing pin (224) allows for an appropriate reading of the thickness of the received tissue, as pin (224) will advance to a position of measurement display (210) correlating with a thickness measurement appropriately measuring the thickness of the tissue compressed between interior surface (204) of end effector (80) and plate (214) of cartridge device (200). Further, removal of pressure from plate (214) may cause pin (224) to move proximally along the horizontal measurement display slot, back toward an initial, zero-pressure (zero tissue thickness) position.

In some versions, cartridge device (200) may include a locking feature (not shown) that is operable to selectively lock pin (224) in position at the measured increment along measurement display (210) such that pin (224) remains in this position after closure trigger (26) is released. Thus, a surgeon may position end effector (80) with cartridge device (200) in the patient, squeeze closure trigger (26) toward handle (25) to measure the thickness of tissue that is positioned between cartridge device (200) and interior surface (204) of shoulder rivet (82), then reposition end effector (80) to a location (e.g., outside of the patient) where it is easier to see the locked location of pin (224) in measurement display (210). In some such versions, the surgeon may even remove cartridge device (200) from end effector (80) to observe the locked position of pin (224) in measurement display (210). By way of example only, a ratcheting locking feature comprising ratchet teeth may be disposed along an exterior wall of pivotable linkage (222), along horizontal linkage (218), and/or elsewhere. As pivotable linkage (222) rotates about pivot pin (225), a pawl (not shown) may slide between the ratchet teeth. A resilient member may bias the pawl into engagement with the teeth, while a button or other feature may be operated to selectively disengage the pawl from the teeth. Other suitable ways in which a ratchet assembly may be provided will be apparent to those of ordinary skill in the art in view of the teachings herein. Similarly, other suitable ways to selectively lock the position of pin (224) will be apparent to those of ordinary skill in the art in view of the teachings herein.

It should be understood that a tissue measurement obtained using cartridge device (200) may allow a user to select an appropriately sized cartridge module (120) to use to sufficiently staple and/or sever the measured tissue in a manner as described above with respect to instrument (20). The appropriately sized cartridge module (120) may be selected from a plurality of cartridge modules (120) including, for example, staples of different heights. Additionally or alternatively, the plurality of cartridge modules (120) may include different sized housings. Cartridge device (200) allows a surgeon to select the cartridge module (120) having the optimal staple height and/or housing size for the particular tissue to be stapled. After use, cartridge device (200) may be removed from end effector (80), the selected cartridge module (120) may be used, and the removed cartridge device (200) may be re-set and reused as described above before the next use of another selected cartridge module (120), which may be used to staple and/or sever another portion of measured tissue.

B. Exemplary Removable Cartridge Device with a Spring Molded Plastic Assembly

Figure 8:
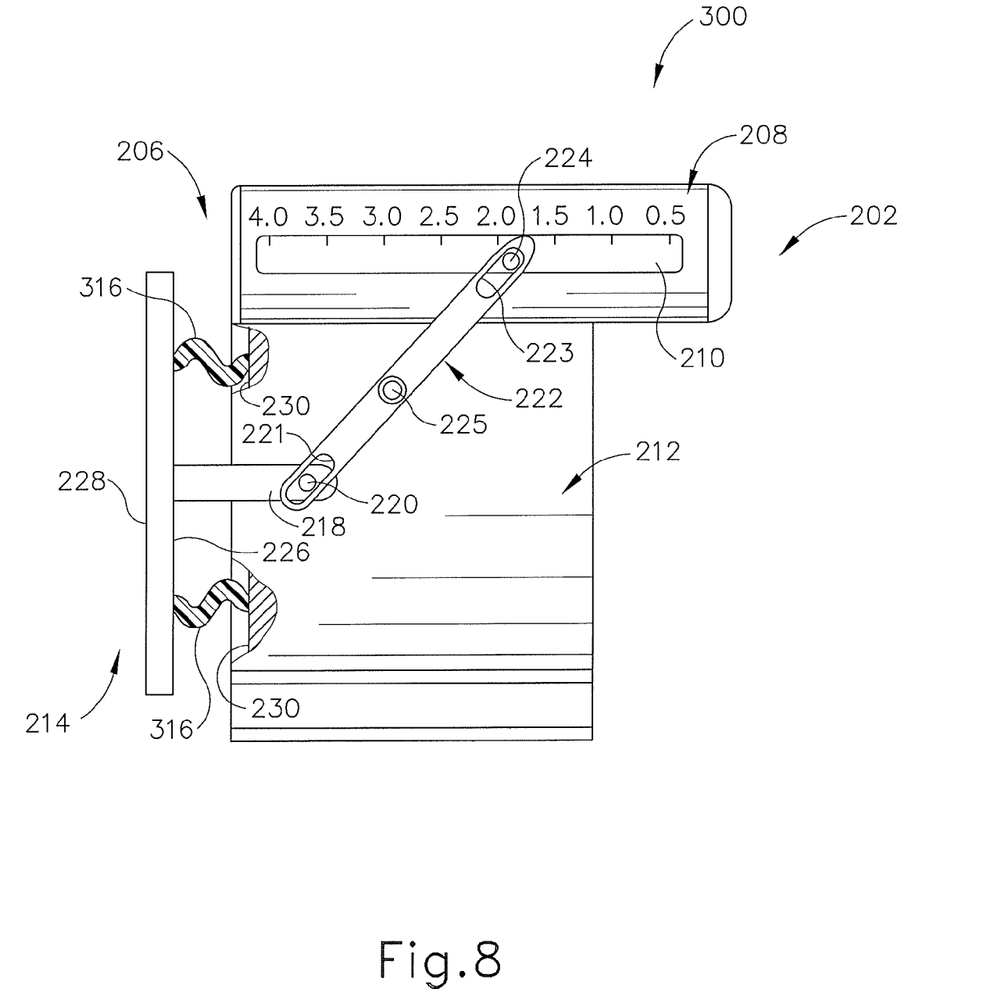
FIG. 8 depicts a side elevation view of an alternative exemplary removable cartridge device to measure tissue thickness.

FIG. 8 shows an exemplary alternative cartridge device (300), which is similar to cartridge device (200) and includes like reference numbers. Cartridge device (300) differs from cartridge device (200) with respect to the plate and biasing member components. As shown in FIG. 8, cartridge device (300) includes plate (214) and molded resilient members (316). Resilient members (316) are molded features of plate (214) and/or cartridge device (300). Thus, plate (214), horizontal linkage (218), and resilient members (316) form a single monolithic piece or component as a homogenous continuum of material (e.g., plastic, etc.). In some versions, resilient members (316), plate (214), and receiving distal surface (230) all form a single monolithic piece or component as a homogenous continuum of material (e.g., plastic, etc.). Resilient members (316) extend between proximal surface (226) of plate (214) and distal surface (230) of cartridge device (300), biasing plate (214) away from distal surface (230). Cartridge device (300) may be operable in the same manner as described above for cartridge device (200).

Figure 9:
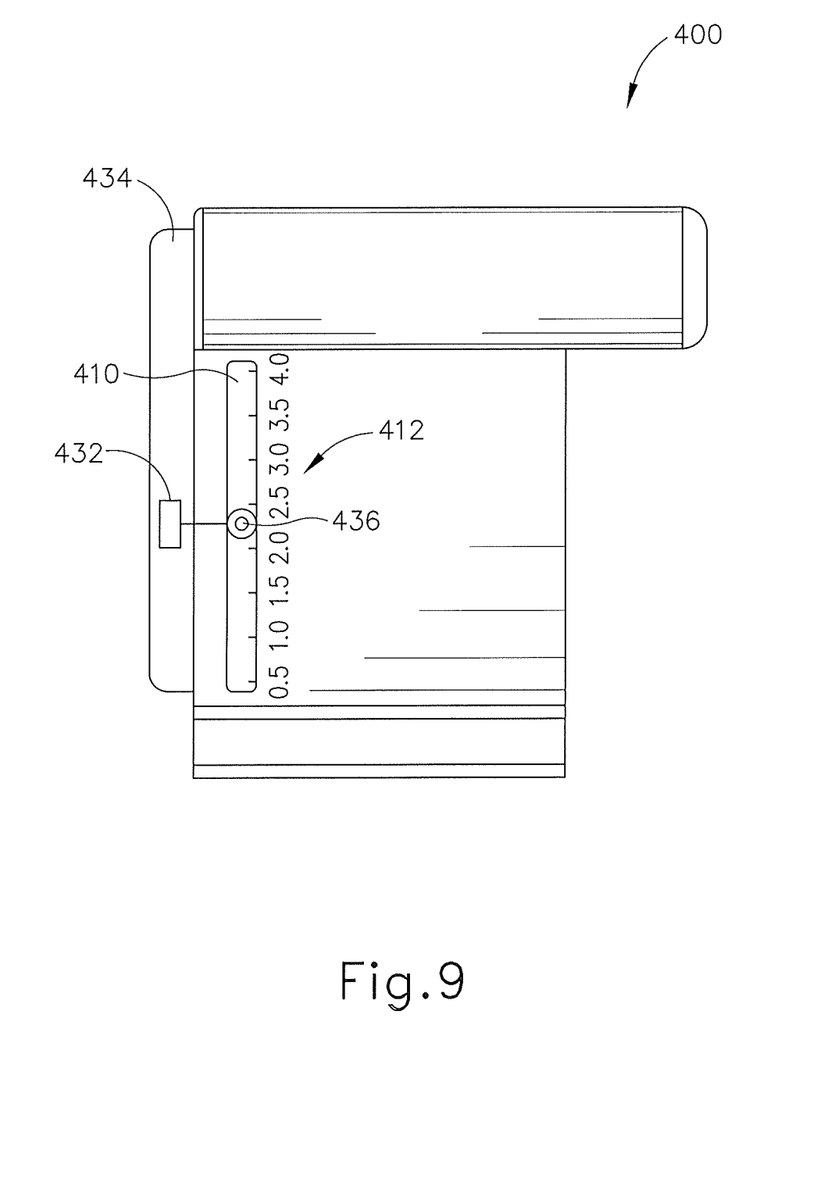
FIG. 9 depicts a side elevation view of another alternative exemplary removable cartridge device to measure tissue thickness.

C. Schematic Representation of an Exemplary Alternative Removable Cartridge Device FIG. 9 shows another exemplary alternative cartridge device (400), which is similar to cartridge devices (200, 300). Cartridge device (400), however, includes a vertical measurement display (410), shown in the present example to include measurements of 0.5 increments on a graduated scale ranging from 0 to 4.0 (though other measurements or increments may be displayed). Cartridge device (400) includes a mechanical gauge assembly (412) that communicates with vertical measurement display (410) via schematically represented link (432) to measure tissue thickness as described above with respect to cartridge device (200). Beyond a mechanical gauge assembly, other indicators apparent to those of ordinary skill in the art in view of the teachings herein may be used to determine approximate tissue thickness for tissue positioned between cartridge device (400) and interior surface (204) of end effector (80). Various suitable components and configurations that may be used as transducers to convert pressure applied to cartridge device (400) into a measurement of tissue thickness will be apparent to those of ordinary skill in the art in view of the teachings herein.

Vertical measurement display (410) is oriented along a distal edge portion of cartridge device (400) in a position substantially parallel to the position against which tissue is received against a pressure measuring device (434) associated with mechanical gauge assembly (412). Vertical measurement display (410) includes pin (436). Pin (436) reacts in response to pressure received against pressure measuring device (434), which is communicated to pin (436) via link (432) to cause pin (436) to move to an appropriate measurement display increment along vertical measurement display (410). Pin (436) thus indicates the thickness of the tissue captured and measured between pressure measuring device (434) and interior surface (204) of end effector (80).

While some configurations for cartridge devices (200, 300, 400) have been described, still other suitable configurations for cartridge devices (200, 300, 400) will be apparent to one of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body having a proximal end and a distal end, with a handle positioned at the proximal end;

(b) a removable insert including a measurement indicator;

(c) an end effector positioned at the distal end of the body, the end effector having a distal interior surface facing the proximal end of the body, the end effector being configured to receive the removable insert; and (d) an actuation feature in communication with the end effector and the removable insert when the removable insert is received in the end effector, the actuation feature being configured to advance the removable insert distally toward the distal interior surface of the end effector;

wherein the measurement indicator of the removable insert is configured to determine thickness of tissue positioned between the removable insert and the distal interior surface of the end effector;

wherein the measurement indicator comprises a mechanical gauge assembly and a measurement display scale, wherein the mechanical gauge assembly is in communication with the measurement display scale, wherein the mechanical gauge assembly further comprises:

(i) a pressure reception component positioned perpendicular to the measurement display scale, (ii) a horizontal linkage coupled to the pressure reception component and extending parallel to the measurement display scale, and (iii) a pivotable linkage having a first end coupled to the horizontal linkage and a second end slidably coupled to the measurement display scale via a first pin, wherein the pivotable linkage is configured to pivot about a point between the first end and the second end, wherein a position of the first pin relative to the measurement display scale provides a measurement of thickness of tissue positioned between the removable insert and the distal interior surface of the end effector.

2. The surgical instrument of claim 1, wherein the mechanical gauge assembly of the removable insert is configured to determine tissue thickness of tissue positioned between the removable insert and the distal interior surface of the end effector, and wherein the measurement display scale is configured to display the determined tissue thickness.

3. The surgical instrument of claim 1, wherein the removable insert comprises a proximal end and a distal end and an insert axis disposed therebetween, wherein the pressure reception component is disposed perpendicular to the insert axis.

4. The surgical instrument of claim 3, wherein the pressure reception component comprises a resiliently biased plate.

5. The surgical instrument of claim 3, wherein the measurement display scale comprises a graduated scale increasing in value from the proximal end to the distal end of the removable insert.

6. The surgical instrument of claim 1, wherein the mechanical gauge assembly comprises a plate and one or more resilient members disposed between the plate and a receiving surface of the removable insert, wherein the plate is configured to compress the one or more resilient members upon application of pressure.

7. The surgical instrument of claim 6, wherein the one or more resilient members comprise springs.

8. The surgical instrument of claim 6, wherein the plate comprises metal.

9. The surgical instrument of claim 6, wherein the plate comprises plastic.

10. The surgical instrument of claim 6, wherein the mechanical gauge assembly further comprises a pivot pin, and a second pin in communication with the measurement display scale and the pivotable linkage.

11. The surgical instrument of claim 10, wherein the second pin is in communication with the horizontal linkage and the pivotable linkage, wherein the pivotal linkage is configured to pivot about the pivot pin upon application of pressure via the horizontal linkage.

12. The surgical instrument of claim 11, wherein the horizontal linkage is configured to proximally advance in response to an applied pressure upon the plate such that the pivotable linkage pivots about the pivot pin and the first pin distally advances along the measurement display scale.

13. A surgical instrument comprising:

(a) a body having a proximal end and a distal end;

(b) a removable insert including a mechanical gauge assembly and a measurement display scale, wherein the mechanical gauge assembly comprises a pin;

(c) an end effector positioned at the distal end of the body, the end effector having a distal interior surface facing the proximal end of the body, the end effector being configured to receive the removable insert; and (d) an actuation feature in communication with the end effector and the removable insert when the removable insert is received in the end effector, the actuation feature being configured to advance the removable insert distally toward the distal interior surface of the end effector;

wherein the mechanical gauge assembly of the removable insert is configured to determine thickness of tissue positioned between the removable insert and the distal interior surface of the end effector, and wherein the measurement display scale is configured to display the determined tissue thickness;

wherein the pin is configured to slide in a proximal direction relative to the measurement display scale in order to provide a measurement of thickness of tissue positioned between the removable insert and the distal interior surface of the end effector;

wherein the measurement display scale comprises a graduated scale increasing in value from the proximal end to the distal end of the removable insert.

14. The surgical instrument of claim 13, wherein the measurement display scale is configured to reset to an initial, zero-pressure value upon removal of the removable insert from the surgical instrument.

15. The surgical instrument of claim 13, wherein the measurement display scale comprises a graduated scale increasing in value in increments of 0.5 from the proximal end to the distal end of the removable insert, wherein the value is in a range of about 0 to 4.0 millimeters.

16. A method of using a surgical instrument including a body having an end effector including a distal interior surface and configured to receive an insert, the insert including a distal surface facing the distal interior surface of the end effector, a mechanical gauge assembly in communication with the distal surface of the insert, and a measurement display scale in communication with the mechanical gauge assembly, the method comprising the steps of:

(a) receiving the insert in the end effector;

(b) positioning tissue between the distal interior surface of the end effector and the distal surface of the insert;

(c) advancing the insert via advancement of an actuation feature to clamp the tissue between the distal interior surface of the end effector and the distal surface of the insert;

(d) applying pressure via the clamped tissue against the distal surface of the insert;

(e) based on the applied pressure, converting the applied pressure via the mechanical gauge assembly into a mechanical measurement of tissue thickness, wherein a reference portion of the mechanical gauge assembly slides in a proximal direction relative to the measurement display scale as the measured tissue thickness decreases; and (f) displaying the measured tissue thickness on the measurement display scale by positioning the reference portion of the mechanical gauge assembly relative to the measurement display scale.

17. The method of claim 16, further comprising the steps of:
(a) removing the insert from the end effector;
(b) based on the measured tissue thickness, selecting a cartridge configured to at least staple tissue having the measured tissue thickness; and
(c) inserting the selected cartridge into the end effector.

* * * * *